United States Patent
Uchida et al.

(10) Patent No.: US 10,900,014 B2
(45) Date of Patent: Jan. 26, 2021

(54) LONG-TERM STORAGE MEDIUM FOR CULTURING OBLIGATE ANAEROBIC BACTERIA OR MICROAEROBIC BACTERIA UNDER AEROBIC ENVIRONMENT, AND METHOD OF DETECTING OBLIGATE ANAEROBIC BACTERIA OR MICROAEROBIC BACTERIA USING SAID MEDIUM

(71) Applicant: Kanto Kagaku Kabushiki Kaisha, Tokyo (JP)

(72) Inventors: Norikuni Uchida, Kanagawa (JP); Akihiko Yokoyama, Isehara (JP)

(73) Assignee: Kanto Kagaku Kabushiki Kaisha, Tokyo (JP)

( * ) Notice: Subject to any disclaimer, the term of this patent is extended or adjusted under 35 U.S.C. 154(b) by 261 days.

(21) Appl. No.: 15/381,585

(22) Filed: Dec. 16, 2016

(65) Prior Publication Data
US 2017/0175074 A1 Jun. 22, 2017

(30) Foreign Application Priority Data
Dec. 18, 2015 (JP) ................. 2015-247778

(51) Int. Cl.
*C12N 1/20* (2006.01)
*C12N 1/38* (2006.01)

(52) U.S. Cl.
CPC ............... *C12N 1/20* (2013.01); *C12N 1/38* (2013.01); *C12N 2500/02* (2013.01); *C12N 2500/38* (2013.01); *C12N 2500/42* (2013.01); *C12N 2500/44* (2013.01)

(58) Field of Classification Search
CPC ..................... C12N 1/20; C12N 1/38
See application file for complete search history.

(56) References Cited

U.S. PATENT DOCUMENTS 4,529,702 A 7/1985 Bryan

FOREIGN PATENT DOCUMENTS

| JP | 2006-254790 A | 9/2006 |
|---|---|---|
| WO | WO 2006/056853 A1 | 6/2006 |
| WO | WO 2013/049039 A1 | 4/2013 |
| WO | WO 2014/064359 A1 | 5/2014 |
| WO | WO 2015/162366 A1 | 10/2015 |
| WO | WO 2015/184454 A1 | 12/2015 |

OTHER PUBLICATIONS

Sapi et al. "Improved Culture Conditions for the Growth and Detection of Borrelia from Human Serum" (2013) Int J Med Sci, vol. 10, 362-376. (Year: 2013).*

Stoenner "Biology of Borrelia hemsii in Kelly Medium", 1974, Applied Microbiology, vol. 28(4): 540-543. (Year: 1974).*

Sigma "BSK-H complete Medium Product Information" (Year: 2018).*

Rothe et al. "A simplified method for cultivation of extreme anaerobic Archaea based on the use of sodium sulfite as reducing agent", 2000 Extremephiles, vol. 4: 247-252. (Year: 2000).*

Cline et al. "New Water-Soluble Phosphines as Reductants of Peptide and Protein Disulphide Bonds: Reactivity and Membrane Permeability" 2004 Biochemistry: vol. 43: 15195-15203. (Year: 2004).*

Crossley et al. "The use of soluble starch medium in the preparation of smooth "O" *Salmonella* antigens." 1946, Journal of Bacteriology, vol. 52, No. 3: 367-371. (Year: 1946).*

Karasawa et al., A defined growth medium for Clostridium difficile. Microbiology. Feb. 1995;141 ( Pt 2):371-5.

Padgett et al., Improving the growth response of *Borrelia* species. Canadian J Mic. 1995;41(11):1031-1034.

Cadnum et al., Sensitive and selective culture medium for detection of environmental Clostridium difficile isolates without requirement for anaerobic culture conditions. J Clin Microbiol. Sep. 2014;52(9):3259-63. doi: 10.1128/JCM.00793-14.

Kamiya et al., Isolation culture of Helicobacter pylori and analysis of virulence factors. Nihon Saikingaku Zasshi (Japanese journal of bacteriology). 2002;57(4):619-655.

Numata et al., Evaluation of recovery methods of Clostridium difficile from environmental surfaces—comparison of spore-recovery techniques and selective media. Kankyo Kansen (Environmental infection). 2004;19(4):475-482.

Sack et al., Isolation of enterotoxigenic Bacteroides fragilis from Bangladeshi children with diarrhea: a controlled study. J Clin Microbiol. Apr. 1994;32(4):960-3.

Shimizu et al., Comparison and improvement of detection media for sublethal injured Clostridium perfringens. Bulletin of Fisheries Sciences. Hokkaido University. Aug. 3, 2009. 59(2):37-42.

EP Communication pursuant to Article 94(3) EPC, dated Apr. 30, 2018. for EP Application No. 16204374.9.

EP Communication pursuant to Article 94(3) EPC, dated Apr. 5, 2019, for EP Application No. 16204374.9, dated Apr. 5, 2019.

Fuentes et al., Growth Characteristics of Clostridium haemolyticum III. Reducing Agents. Rev Salud Anim. 1984;6(1):29-38. Ediciones Cubanas, Havana, Cuba.

Kawabata, Studies on the sulfite reduction test for Clostridia. Microbiol Immunol. 1980;24(4):271-9.

Krieg et al., Microaerophily and oxygen toxicity. Annu Rev Microbiol. 1986;40:107-30.

(Continued)

*Primary Examiner* — Teresa E Knight
(74) *Attorney, Agent, or Firm* — Wolf, Greenfield & Sacks, P.C.

(57) ABSTRACT

[Problem] To provide a medium suitable for long-term storage, i.e., that ensures sufficient quality retention period, for growing obligate anaerobic bacteria or microaerobic bacteria under aerobic environment, and to provide a method of easily detecting obligate anaerobic bacteria or microaerobic bacteria using said medium.

[Means for solving the problem] A long-term storage medium comprising dithiothreitol and/or ascorbic acid as a reducing agent in a basal medium, for culturing obligate anaerobic bacteria or microaerobic bacteria under aerobic environment, and a method of detecting obligate anaerobic bacteria or microaerobic bacteria using said medium.

14 Claims, 2 Drawing Sheets

(56) References Cited

OTHER PUBLICATIONS

Lagier et al., Current and past strategies for bacterial culture in clinical microbiology. Clin Microbiol Rev. Jan. 2015;28(1):208-36. doi: 10.1128/CMR.00110-14.

Pollack et al., Standardization of medium for culturing Lyme disease spirochetes. J Clin Microbiol. May 1993;31(5):1251-5.

Serata et al., Roles of thioredoxin and thioredoxin reductase in the resistance to oxidative stress in Lactobacillus casei. Microbiology. Apr. 2012;158(Pt 4):953-62. doi: 10.1099/mic.0.053942-0. Epub Feb. 2, 2012.

Tang et al., Characterization of the BatI (Bacteroides aerotolerance) operon in Bacteroides fragilis: isolation of a B. fragilis mutant with reduced aerotolerance and impaired growth in in vivo model systems. Mol Microbiol. Apr. 1999;32(1):139-49.

Okazaki, Studies on the growth of anaerobic bacteria in the medium containing different reducing agents. Jap. J. of Bact. 1955;2:129-133.

\* cited by examiner

Fig. 1A
Prior to culturing

Fig. 1B
After culturing

— A mass of bacteria

Fig. 2A The medium of Example 2

$3 \times 10^6$   $3 \times 10^5$   $3 \times 10^3$   30   3   (cfu)

Fig. 2B The medium of Comparative Example 2

$3 \times 10^6$   $3 \times 10^5$   $3 \times 10^3$   30   3   (cfu)

LONG-TERM STORAGE MEDIUM FOR CULTURING OBLIGATE ANAEROBIC BACTERIA OR MICROAEROBIC BACTERIA UNDER AEROBIC ENVIRONMENT, AND METHOD OF DETECTING OBLIGATE ANAEROBIC BACTERIA OR MICROAEROBIC BACTERIA USING SAID MEDIUM

FIELD

The present invention relates to a long-term storage medium for culturing obligate anaerobic bacteria or microaerobic bacteria under aerobic environment, and a method of detecting obligate anaerobic bacteria or microaerobic bacteria using said medium.

BACKGROUND

A culture method is one of effective methods for identifying causative bacteria of infectious diseases. However, in addition to bacteria that can be cultured under aerobic environment, there are bacteria that require anaerobic environment or microaerobic environment for culturing.

For example, *Clostridium diffcile* (hereinafter, *C. difficile*) that is a causative bacterium of pseudomembranous colitis, is an obligate anaerobic bacterium, and because it cannot grow in the presence of oxygen, it is essential to culture it under anaerobic environment. In addition, *Clostridium perfringens* (hereinafter, *C. perfringens*) and *Bacteroides fragilis* (hereinafter, *B. fragilis*) that are causative bacteria of food poisoning are also obligate anaerobic bacteria, and it is essential to culture them under anaerobic environment. Regarding *Helicobacter pylori* (hereinafter, *H. Pylori*) that is said to be associated with digestive system disorders, while anaerobic environment is not required for culturing, it is essential to culture it under microaerobic environment.

Although culture and detection of these bacteria are strongly required, due to the difficulty and complication in the culture, development of a detection method using novel culturing is underway. For example, in Non-Patent Literature 1, various media for culturing *C. Difficile* under anaerobic environment are described, and it is described that the detection sensitivity for *C. difficile* differs depending on the type or composition of components contained in each media. However, culturing *C. difficile* using said media requires anaerobic environment, so that special equipment and special knowledge and techniques for culturing under anaerobic environment are necessary; therefore, application of the detection method of *C. difficile* using the media described in Non-Patent Literature 1 for easy detection of *C. difficile* in clinical settings such as hospitals is difficult.

In addition, culturing *C. perfringens* (Non-Patent Literature 2) and *B. fragilis* (Non-Patent Literature 3) under anaerobic environment using special equipment is described; in the both cases of *C. perfringens* and *B. fragilis*, special equipment and special knowledge and techniques for culturing under anaerobic environment are required as in the case of culturing the above *C. difficile*. Moreover, in Non-Patent Literature 4, culturing *H. pylori* using special equipment under microaerobic environment is described; here, special equipment and special knowledge and techniques are required for such microaerobic culture.

Meanwhile, in Non-Patent Literature 5, a medium comprising thioglycolic acid and L-cysteine as a reducing agent for culturing *C. difficile* under aerobic environment is described. By using such a medium, the use of special equipment and special knowledge and techniques for culturing *C. difficile* under anaerobic environment is not necessary, and therefore easy detection of *C. difficile* using said medium becomes possible.

CITATION LIST

Non-Patent Literature

[NPL1] Noboru Numata, Kikuyoshi Yoshida. Ham Kato, Nobuchika Arakawa: "Study method of *Clostridium difficile* contamination in environment—Comparison of harvesting methods and separation media of bacteria—", Kankyo Kansen (Environmental infection), Vol. 19, no. 4, 475-482, 2004 (in Japanese).

[NPL2] Shigemasa Shimizu, Asuka Horiguchi, Hiroshi Yamazaki, Yuji Kawai: "Comparison and improvement of detection media of heat-damaged *Clostridium perfringens*", Hokkaido University Fisheries Bulletin, Vol. 52, no. 2, 37-42, 2009 (in Japanese).

[NPL3] R. Bradley Sack, M. John Albert, K. Alam. P. K. B. Neogi. M. S. Akbar: "Isolation of Enterotoxigenic *Bacteroides fragilis* from Bangladeshi Children with Diarrhea: a Controlled Study" J. Clin. Microbiol., 32(4): 960-963, 1994.

[NPL4] Shigeru Kamiya, Haruhiko Taguchi: "Separation culture of *Helicobacter pylori* and analysis of virulence factors" Nihon Saikingaku Zasshi (Japan bacteriology magazine), Vol. 57, no. 4, 619-655, 2002 (in Japanese).

[NPL5] Cadnum J L, Hurless K N, Deshpande A, Nerandzic M M, Kundrapu S, Donskey C J. "Sensitive and Selective Culture Medium for Detection of Environmental *Clostridium difficile* Isolates without Requirement for Anaerobic Culture Conditions" J. Clin. Microbiol, 52(9): 3259-3263, 2014.

SUMMARY

Problems to be Solved by the Invention

As noted above, in Non-Patent Literature 5, while there is a description of a medium comprising thioglycolic acid and L-cysteine as a reducing agent for culturing *C. difficile* under aerobic environment, it is also described that after two weeks from the preparation of said medium, the detection sensitivity for *C. difficile* gradually decreases. Therefore, said medium is not suitable for long-term storage, and it is difficult to secure sufficient quality-retaining period; and therefore commercializing said medium for distribution on the market is not practical. In addition, said medium is a medium for culturing *C. difficile* under aerobic environment, and a medium for culturing other obligate anaerobic bacteria such as *C. perfringens* and *B. fragilis* and microaerobic bacteria such as *H. pylori*, under aerobic environment, are not known.

Thus, the present invention provides a medium suitable for long-term storage, that is, a medium that ensures sufficient quality-retaining period, for culturing obligate anaerobic bacteria or microaerobic bacteria under aerobic environment, and also provides a method of easily detecting obligate anaerobic bacteria or microaerobic bacteria using said medium.

In this specification, "a long-term storage medium for culturing obligate anaerobic bacteria or microaerobic bacteria under aerobic environment" according to the present invention is simply referred to as "the medium of the present invention".

Means for Solving the Problems

The present inventors have found for the first time that, by adding dithiothreitol and/or ascorbic acid as a reducing agent to a basal medium, the medium can be stored for a long time of at least 4 months. In view of the above problems, the present inventors have realized easy culturing of obligate anaerobic bacteria or microaerobic bacteria without special equipment and special knowledge and technologies, as follows: using a medium in which dithiothreitol and/or ascorbic acid as a reducing agent is added to a basal medium, to which selected growth-supporting agents and/or antibacterial agents are also added with consideration given to each characteristic of the detection targets obligate anaerobic bacteria or microaerobic bacteria, then obligate anaerobic bacteria such as C. difficile, C. perfringens and B. fragilis as well as microaerobic bacteria such as H. pylori are cultured under aerobic environment; and thus the present inventors have completed the present invention.

Namely, the present invention relates to the following:

[1] A long-term storage medium comprising dithiothreitol and/or ascorbic acid as a reducing agent in a basal medium, for culturing obligate anaerobic bacteria or microaerobic bacteria under aerobic environment.

[2] The medium according to [1], wherein the concentration of dithiothreitol is 0.075-1.5 g/L, and the concentration of ascorbic acid is 0.075-3.6 g/L.

[3] The medium according to [1] or [2], further comprising tris(2-carboxyethyl)phosphine hydrochloride as a reducing agent.

[4] The medium according to [3], wherein the concentration of tris(2-carboxyethyl)phosphine hydrochloride is 0.1-2.0 g/L.

[5] The medium according to any one of [1]-[4], further comprising at least one first growth-supporting agent selected from the group consisting of glycine, magnesium sulfate and sodium hydrogen carbonate.

[6] The medium according to [5], wherein the concentration of glycine is 0.1-2.0 g/L, the concentration of magnesium sulfate is 0.01-1.0 g/L, and the concentration of sodium hydrogen carbonate is 0.5-4.0 g/L.

[7] The medium according to any one of [1]-[6], further comprising at least one second growth-supporting agent selected from the group consisting of arginine, sodium sulfite, potassium sulfite, sodium pyruvate, potassium pyruvate and soluble starch.

[8] The medium according to [7], wherein the concentration of arginine is 0.1-2.0 g/L, the concentration of sodium sulfite is 0.01-1.0 g/L, the concentration of sodium pyruvate is 0.1-2.0 g/L, and the concentration of soluble starch is 1.0-8.0 g/L.

[9] The medium according to any one of [1]-[8], wherein the basal medium comprises at least one antibacterial agent selected from the group consisting of cycloserine, cephalosporin antibacterial agents, glycopeptide antibacterial agents, diaminopyrimidine antibacterial agents, polyene antibacterial agents, polypeptide antibacterial agents and aminoglycoside antibacterial agents.

[10] The medium according to [9], wherein the cephalosporin antibacterial agent is cefoxitin, the glycopeptide antibacterial agent is vancomycin, diaminopyrimidine antibacterial agent is trimethoprim, polyene antibacterial agent is amphotericin B, polypeptide antibacterial agent is polymyxin B, and, aminoglycoside antibacterial agent is gentamicin.

[11] The medium according to any one of [1]-[10], which is a semi-fluid medium or a liquid medium.

[12] A method of detecting obligate anaerobic bacteria or microaerobic bacteria using the medium according to any one of [1]-[11].

[13] The method according to [12], wherein biological samples and/or environmental samples are the subject.

Advantageous Effects of Invention

The medium of the present invention can ensure sufficient quality-retaining period, because it can be stored for a long period of time of at least 4 months by comprising dithiothreitol and/or ascorbic acid as a reducing agent, and it can be commercialized and distributed on the market. In addition, using said medium, it is possible to easily detect obligate anaerobic bacteria or microaerobic bacteria by culturing the obligate anaerobic bacteria or microaerobic bacteria under aerobic environment. Furthermore, by adding a growth-supporting agent in said medium, it is possible to improve the detection sensitivity of obligate anaerobic bacteria or microaerobic bacteria, to prevent false negatives, and to diagnose properly by determining whether or not the cause of a disease is obligate anaerobic bacteria or microaerobic bacteria. It should be noted that, by making said medium as a semi-fluid medium or a liquid medium, it is also possible to subject genes and toxins derived from obligate anaerobic bacteria or microaerobic bacteria to various molecular biological tests, after culturing the obligate anaerobic bacteria or microaerobic bacteria.

DESCRIPTION OF EMBODIMENTS

Hereinafter, the present invention will be described in detail based on preferred embodiments of the present invention.

<Medium of the Present Invention>

The medium of the present invention comprises, as a base, a basal medium comprising at least peptone, sugars, salts and antibacterial agents, and optionally comprising, for example, agar, an acid-base indicator, and a reducing agent such as cysteine, to which dithiothreitol and/or ascorbic acid or a salt thereof, as well as tris(2-carboxyethyl)phosphine hydrochloride as a reducing agent are added; and said medium is a long-term storage medium for culturing obligate anaerobic bacteria or microaerobic bacteria under aerobic environment, without using special equipment and special knowledge and technologies.

<Obligate Anaerobic Bacteria and Microaerobic Bacteria>

In the present invention, obligate anaerobic bacteria refer to bacteria which cannot grow in the presence of oxygen, and the examples include, but are not limited to, C. difficile, C. perfringens, B. fragilis and the like. In addition, in the present invention, microaerobic bacteria refer to bacteria which require oxygen for culturing, but the concentration of the oxygen is much lower than that in atmospheric environment, and the examples include, but are not limited to, *H. pylori* and the like. There are various kinds of strains of these obligate anaerobic bacteria or microaerobic bacteria, but the present invention is not limited thereto.

Examples of obligate anaerobic bacteria include *Clostridium* genus and *Bacteroides* genus and the like, and examples of microaerobic bacteria include *Helicobacter* genus and the like. *Clostridium* genus includes *C. difficile* and *C. perfringens*, and *Bacteroides* genus includes *B. fragilis*, and *Helicobacter* genus includes *H. pylori*.

<Culture Under Aerobic Environment, Anaerobic Environment or Microaerobic Environment>

In the present invention, culture under aerobic environment refers to the culture in an incubator, etc. under the environment that does not use anaerobic jar, anaerobic pack and/or microaerobic pack. When culturing obligate anaerobic bacteria or microaerophilic bacteria under aerobic environment becomes possible, obligate anaerobic bacteria or microaerophilic bacteria can be easily detected, since special equipment and special knowledge and technologies for culturing under anaerobic environment are not necessary. In addition, in the present invention, culture under anaerobic environment refers to the culture in an incubator, etc., under the environment using anaerobic jar and anaerobic pack. Furthermore, in the present invention, culture under microaerobic environment refers to the culture in an incubator, etc., under the environment using anaerobic jar and microaerobic pack. Examples of anaerobic pack include oxygen-absorbing and carbon-dioxide-generating agents such as Anaero Pack®-Anaero (Mitsubishi Gas Chemical Company, Inc.), which is used to maintain an anaerobic environment in an anaerobic jar; in contrast, examples of microaerobic pack include oxygen-absorbing and carbon-dioxide-generating agents such as Anaero Pack®-MicroAero (Mitsubishi Gas Chemical Company, Inc.), which is used to maintain a microaerobic environment in an anaerobic jar.

<Basal Medium>

In the present invention, peptones are amino acids and low-molecular-weight peptides formed by the hydrolysis of protein, and any peptones comprising basic nutrients used for general microbial culture may be used; one kind of peptone or two or more kinds of peptones in combination may be used. Such nutrients can be understood by those skilled in the art.

Examples of saccharides used in the present invention include monosaccharides such as glucose and fructose, disaccharides such as lactose, as well as sugar alcohols such as mannitol.

Examples of salts include sodium chloride, potassium dihydrogen phosphate, disodium hydrogen phosphate, dipotassium hydrogen phosphate, and sodium taurocholate, etc.

Examples of antibacterial agents used in the present invention include cephalosporin antibacterial agents, glycopeptide antibacterial agents, diaminopyrimidine antibacterial agents, polyene antibacterial agents, polypeptide antibacterial agents, monobactam antibacterial agents, oxacephem antibacterial agents, aminoglycoside antibacterial agents, fosfomycin and cycloserine, etc., but are not limited thereto. Cephalosporin antibacterial agents include cefsulodin, cefaclor, cefotetan, cefoxitin, cefprozil, cefuroxime, loracarbef, cefdinir, cefditoren, cefixime, cefoperazone, cefotaxime, cefpodoxime, ceftazidime, ceftibuten, ceftizoxime, ceftriaxone and cefepime; glycopeptide antibacterial agents include vancomycin and teicoplanin; diaminopyrimidine antibacterial agents include trimethoprim; polyene antibacterial agents include amphotericin B, nystatin and natamycin; polypeptide antibacterial agents include bacitracin, colistin and polymyxin B; monobactam antibacterial agents include aztreonam; oxacephem antibacterial agents include moxalactam (latamoxef); and aminoglycoside antibacterial agents include streptomycin, kanamycin, gentamicin, tobramycin, amikacin, dibekacin and arbekacin. Cephalosporin antibacterial agents, monobactam antibacterial agents, oxacephem antibacterial agents and aminoglycoside antibacterial agents are used as, for example, antibacterials, and polyene antibacterial agents are used as, for example, antifungals.

As the antibacterial agents used in the present invention, preferably, antibacterial agents that can specifically suppress the growth of contaminating bacteria without affecting the growth of bacteria to be detected are selected. For example, when detecting *C. difficile*, cycloserine and/or cefoxitin may be selected; when detecting *C. perfringens*, cycloserine may be selected; when detecting *B. fragilis*, vancomycin and/or gentamicin may be selected; when detecting *H. pylori*, trimethoprim, vancomycin and/or amphotericin B may be selected. In addition, for example, when detecting *Campylobacter jejuni* which is a microaerobic bacterium and a causative bacterium for food poisoning and, with which association with Guillain-Barre syndrome is suspected and a number of infection cases via poultry have been reported, cefoperazone, vancomycin, and cycloheximide may be selected. When detecting *Streptococcus agalactiae*, which is a microaerobic bacterium causing mother-to-child vertical infection, and is known to induce bacterial meningitis having high mortality in neonates, trimethoprim and amphotericin B may be selected. When detecting *Fusobacterium necrophorum*, which is an obligate anaerobic bacterium and one of the bacteria causing Lemierre's syndrome, erythromycin, vancomycin and amphotericin B may be selected.

As described above, the basal medium may further comprise agar. The concentration of agar is, from the viewpoint of good growth-supporting ability for obligate anaerobic bacteria or microaerobic bacteria and ease of handling of culture solutions after culturing, preferably 0.0-7.5 g/L, more preferably 0.0-3.0 g/L, and particularly preferably 0.0-1.5 g/L. In addition, the medium of the present invention may be a semi-fluid medium or a liquid medium. This is because recovery of obligate anaerobic bacteria or microaerobic bacteria from a semi-fluid medium or a liquid medium is easier than recovery of the same bacteria from a solid medium, and moreover, by directly subjecting the recovered bacteria to various molecular biological tests, detection of genes and/or toxins derived from said bacteria can be easier. In particular, the medium of the present invention is preferably a liquid medium. This is because recovery of obligate anaerobic bacteria or microaerobic bacteria with higher bacteria density from a liquid medium is easier, compared to the recovery of the same bacteria from a semi-fluid medium, and by directly subjecting the recovered bacteria to various molecular biological tests, detection of genes and/or toxins derived from said bacteria can be much easier when compared to the case of semi-fluid medium. Furthermore, by using the liquid medium of the present invention, it becomes possible to freeze-store said medium, allowing to further extend the quality-retaining period.

Examples of such molecular biological tests include immunological tests and genetic tests, and any general immunological tests and genetic tests may be employed in the present invention. Examples of immunological tests include enzyme-linked immunosorbent assay (ELISA, EIA), fluorescence immunoassay (FIA), radioimmunoassay (RIA), luminescence immunoassay (LIA), enzyme labeled antibody method, fluorescent antibody method, immunochromatographic method (immunochromatography), filter antigen assay, turbidimetric immunoassay, latex turbidimetry, latex agglutination assay, hemagglutination reaction or particle aggregation reaction and the like; from the viewpoint of contribution to rapid diagnosis, immunochromatography is preferred. Examples of genetic tests include amplification, quantification and/or detection of genes of interest or fragments thereof by a variety of nucleic acid amplification techniques such as PCR, or determining genetic sequences by sequencing, and the like.

As described above, the basal medium may further comprise an acid-base indicator. Examples of acid-base indicator include those having a color transition range from neutral to basic, such as bromothymol blue, phenol red, neutral red, naphtholphthalein, and cresol red. As the acid-base indicator, from the viewpoint of visibility, neutral red is preferred. In the medium comprising neutral red, the color changes from red to yellow as obligate anaerobic bacteria such as $C.$ $difficile$, $C.$ $perfringens$, and $B.$ $fragilis$ grow and the pH of the medium changes from neutral to basic; accordingly, said obligate anaerobic bacteria can be easily detected from such color change.

<Reducing Agent>

The reducing agent used in the present invention includes tris(2-carboxyethyl)phosphine hydrochloride, in addition to dithiothreitol and/or ascorbic acid, and from the viewpoint of growth inhibiting ability against foreign bacteria, a combination of dithiothreitol and tris(2-carboxyethyl)phosphine hydrochloride is preferred. The concentration of dithiothreitol is, from the viewpoint of growth-supporting ability for obligate anaerobic bacteria or microaerobic bacteria, preferably 0.075-1.5 g/L, more preferably 0.16-1.2 g/L, and particularly preferably 0.6-0.9 g/L. In addition, the concentration of ascorbic acid is, from the viewpoint of growth-supporting ability for obligate anaerobic bacteria or microaerobic bacteria, preferably 0.075-3.6 g/L, more preferably 0.16-2.7 g/L, and particularly preferably 0.32-1.8 g/L. The concentration of tris(2-carboxyethyl)phosphine hydrochloride is, from the viewpoint of growth-supporting ability for obligate anaerobic bacteria or microaerobic bacteria, preferably 0.1-2.0 g/L, more preferably 0.25-1.5 g/L, and particularly preferably 0.5-1.2 g/L. Moreover, as a reducing agent used in the present invention, in addition to those described above, cysteine and/or thioglycolic acid, etc., may be optionally added to the basal medium.

<Growth-Supporting Agent>

The medium of the present invention may further comprise a growth-supporting agent, thereby improving the detection sensitivity of obligate anaerobic bacteria or microaerobic bacteria. Examples of growth-supporting agent to be used in the present invention include a first growth-supporting agent selected from the group consisting of glycine, magnesium sulfate and sodium hydrogen carbonate, and a second growth-supporting agent selected from the group consisting of arginine, sodium sulfite, potassium sulfite, sodium pyruvate, potassium pyruvate and soluble starch. The concentration of glycine is, from the viewpoint of growth-supporting ability for obligate anaerobic bacteria or microaerobic bacteria, preferably 0.1-2.0 g/L, more preferably 0.25-1.5 g/L, and particularly preferably 0.5-1.2 g/L. The concentration of magnesium sulfate is, from the viewpoint of growth-supporting ability for obligate anaerobic bacteria or microaerobic bacteria, preferably 0.01-1.0 g/L, more preferably 0.05-0.5 g/L, and particularly preferably 0.075-0.25 g/L. The concentration of sodium hydrogen carbonate is, from the viewpoint of growth-supporting ability for obligate anaerobic bacteria or microaerobic bacteria, preferably 0.5-4.0 g/L, more preferably 0.75-3.0 g/L, and particularly preferably 1.0-2.0 g/L. The concentration of arginine is, from the viewpoint of growth-supporting ability for obligate anaerobic bacteria or microaerobic bacteria, preferably 0.1-2.0 g/L, more preferably 0.25-1.5 g/L, and particularly preferably 0.5-1.2 g/L. The concentration of sodium sulfite is, from the viewpoint of growth-supporting ability for obligate anaerobic bacteria or microaerobic bacteria, preferably 0.01-1.0 g/L, more preferably 0.05-0.5 g/L, and particularly preferably 0.075-0.25 g/L. The concentration of sodium pyruvate is, from the viewpoint of growth-supporting ability for obligate anaerobic bacteria or microaerobic bacteria, preferably 0.1-2.0 g/L, more preferably 0.25-1.5 g/L, and particularly preferably 0.5-1.2 g/L. The concentration of soluble starch is, from the viewpoint of growth-supporting ability for obligate anaerobic bacteria or microaerobic bacteria, preferably 1.0-8.0 g/L, more preferably 2.0-6.0 g/L, and particularly preferably 4.0-5.0 g/L.

<Preparation Method of Medium for $C.$ $difficile$ of the Present Invention and Method to Use the Same>

$C.$ $difficile$ that can be cultured and detected using the medium of the present invention under aerobic environment is not limited to particular strains. The medium of the present invention is a medium for growing $C.$ $difficile$ under aerobic environment, which is suitable for long-term storage, i.e., which ensures sufficient quality-retaining period.

The medium of the present invention can be prepared as follows: similar to ordinary culture media, each of the components except antibacterial agents that are said to be weak to heat is dissolved in water, etc., steam sterilized, and cooled to a suitable temperature; then antibacterial agents and others are added thereto. Samples can be inoculated directly to the medium of the present invention. The medium of the present invention can culture $C.$ $difficile$ under aerobic environment in a temperature range of 20-40° C. Such temperature range is, from the viewpoint of growth rate of $C.$ $difficile$, preferably 25-39° C., more preferably 30-39° C. and particularly preferably 35-38° C. Such culturing is carried out for, from the viewpoint of growth amount of $C.$ $difficile$, preferably 16-72 h, more preferably 16-42 h, and particularly preferably from 18-38 h. Upon storage of the medium of the present invention, when the medium of the present invention is a semi-fluid medium containing agar, from the viewpoint of long-term storage, the present medium is stored by preferably refrigeration at 2-10° C., more preferably refrigeration at 2-9° C., and particularly preferably refrigeration at 2-8° C. When the medium of the present invention is a liquid medium, from the viewpoint of long-term storage, the present medium is stored by preferably freezing at −4 to −80° C., more preferably freezing at −4 to −40° C., and particularly preferably freezing at −10 to −20° C.

<Detection Method of $C.$ $difficile$>

Figure 1A:
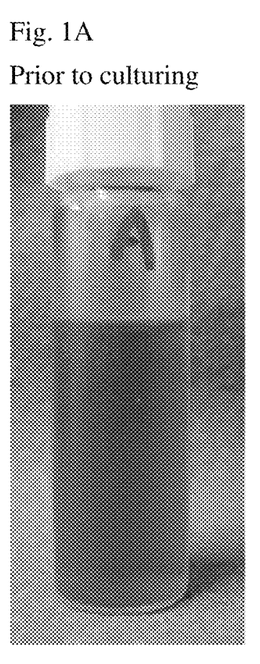
FIGS. 1A and 1B show the medium of Example 2, prior to culturing C. difficile under aerobic environment (FIG. 1A) and after culturing under aerobic environment (FIG. 1B). As the bacteria grow, the color of the medium changes from red to yellow, and a mass of bacteria can be visually confirmed.
Figure 1B:
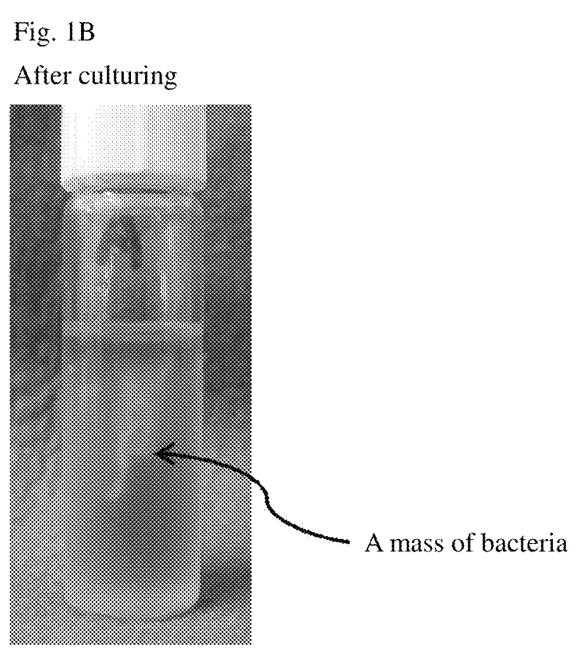

In the method of detecting $C.$ $difficile$ of the present invention, for example as $C.$ $difficile$ grows, amino acids contained in the medium of the present invention are consumed and the pH of the medium changes from neutral to basic, resulting in the color change of an acid-base indicator, and $C.$ $difficile$ can be easily detected from this color change. For example, when using neutral red as the acid-base indicator in the medium of the present invention, when pH changes from neutral to basic, the color of said medium changes from red to yellow, and *C. difficile* can be easily detected from such color change (FIGS. 1A and 1B).

As a sample that can be used in the present invention, any samples that possibly contain *C. difficile* can be used, such as biological samples derived from feces or perianal or rectal inner wall of a human or animal, or environmental samples derived from any locations in a hospital, foods, drinks and tap water, etc.; preferably, the sample is feces that is easy to collect. Methods for collecting these specimens are not particularly limited, and any known methods may be employed. Specifically, a method using a swab or pipette is frequently used.

<Diagnosis Method of Disease Associated with *C. difficile*>

The present invention also encompasses a method of diagnosing or a method to provide useful information for diagnosis, comprising at least a step of selectively growing *C. difficile* by contacting the medium of the invention with biological samples, and further comprising a step of determining presence/absence of toxins produced by the grown *C. difficile* (such as toxin A and B). With such methods, presence/absence of *C. difficile* in the sample can be determined by selectively growing *C. difficile*, thereby diagnosing or providing useful information for diagnosis of whether or not the cause of the disease is *C. difficile*. With such methods, *C. difficile* can be detected with high sensitivity by a simple operation, compared to conventional antigen test method wherein toxins produced by *C. difficile* in a specimen are detected, and therefore, sensitivity of the subsequent detection of toxins can be remarkably improved. Furthermore, while results of a conventional antigen test may be false-negative due to low level of detection sensitivity, in the diagnosis method using the present invention, toxins can be detected while preventing false-negative results, by means of the following procedure: *C. difficile* is grown in the present medium, and presence/absence of *C. difficile* in a sample is determined by its high-sensitivity detection, then after confirmation of the growth of *C. difficile*, the above-mentioned conventional antigen test for toxin detection is carried out; thus, the test of high-concentration toxins produced by *C. difficile* grown in the medium is carried out, instead of the direct test of the above feces, and therefore toxins can be detected while preventing false-negative results. Accordingly, proper diagnosis can be made based on the correct determination of whether or not the cause of the disease is *C. difficile*.

Meanwhile, there is a method of using a conventional detection medium for *C. difficile*, such as CCFA medium (Nippon Becton Dickinson Co., Ltd.) and others; in this method, a specimen is smeared on the medium and cultured under anaerobic environment using special equipment as well as special knowledge and technologies, and the *C. difficile* grown on the medium is scraped with a platinum loop, etc., suspended in a diluent, etc., which is then subjected to an antigen test; this operation is very complicated. In particular, the facts that colonies of *C. difficile* gown on a CCFA medium and others are hardly scraped, and that the scraped colonies are hardly suspended in a diluent, make the operation more complicated. In contrast, when using the media of the present invention, the culture solution after culturing under aerobic environment is suspended in a diluent using a pipette, etc., which is then used for an antigen test; thus the operation is very simple and there is no need for cumbersome operation such as scraping of colonies.

<Preparation Method of Medium for *C. perfringens* of the Present Invention and Method to Use the Same>

*C. perfringens* that can be cultured and detected using the medium of the present invention under aerobic environment is not limited to particular strains. The medium of the present invention is a medium for growing *C. perfringens* under aerobic environment, which is suitable for long-term storage. i.e., which ensures sufficient quality-retaining period.

The medium of the present invention can be prepared as follows: similar to ordinary culture media, each of the components except antibacterial agents that are said to be weak to heat is dissolved in water, etc., steam sterilized, and cooled to a suitable temperature; then antibacterial agents and others are added thereto. Samples can be inoculated directly to the medium of the present invention. The medium of the present invention can culture *C. perfringens* under aerobic environment in a temperature range of 30-40° C. Such a temperature range is, from the viewpoint of growth rate of *C. perfringens*, preferably 32-39° C. more preferably 34-39° C., and particularly preferably 35-37° C. Such culturing is carried out for, from the viewpoint of growth amount of *C. perfringens*, preferably 16-72 h, more preferably 16-42 h. and particularly preferably from 18-24 h. Upon storage of the medium of the present invention, when the medium of the present invention is a semi-fluid medium containing agar, from the viewpoint of long-term storage, the present medium is stored by preferably refrigeration at 2-10° C. more preferably refrigeration at 2-9° C., and particularly preferably refrigeration at 2-8° C. When the medium of the present invention is a liquid medium, from the viewpoint of long-term storage, the present medium is stored by preferably freezing at −4 to −80° C., more preferably freezing at −4 to −40° C., and particularly preferably freezing at −10 to −20° C.

<Detection Method of *C. perfringens*>

In the method of detecting *C. perfringens* of the present invention, for example as *C. perfringens* grows, amino acids contained in the medium of the present invention are consumed and the pH of the medium changes from neutral to basic, resulting in the color change of an acid-base indicator, and *C. perfringens* can be easily detected from this color change. For example, when using neutral red as the acid-base indicator in the medium of the present invention, when the pH changes from neutral to basic, the color of said medium changes from red to yellow, and *C. perfringens* can be easily detected from such color change.

As a sample that can be used in the present invention, any samples that possibly contain *C. perfringens* can be used, such as biological samples derived from feces or perianal or rectal inner wall of a human or animal, or environmental samples derived from any locations in a hospital, foods, drinks and tap water, etc.; preferably, the sample is feces that is easy to collect or foods. Methods for collecting these specimens are not particularly limited, and any known methods may be employed.

<Diagnosis Method of Disease Associated with *C. perfringens*>

The present invention also encompasses a method of diagnosing or a method to provide useful information for diagnosis, comprising at least a step of selectively growing *C. perfringens* by contacting the medium of the invention with biological samples. With such methods, by determining presence/absence of *C. perfringens* in a sample, for example, it is possible to diagnose if the cause of the disease is *C. perfringens* or not.

<Preparation Method of Medium for *B. fragilis* of the Present Invention and Method to Use the Same>

*B. fragilis* that can be cultured and detected using the medium of the present invention under aerobic environment is not limited to particular strains. The medium of the present invention is a medium for growing *B. fragilis* under aerobic environment, which is suitable for long-term storage, i.e., which ensures sufficient quality-retaining period.

The medium of the present invention can be prepared as follows: similar to ordinary culture media, each of the components except antibacterial agents that are said to be weak to heat is dissolved in water, etc., steam sterilized, and cooled to a suitable temperature; then antibacterial agents and others are added thereto. Samples can be inoculated directly to the medium of the present invention. The medium of the present invention can culture *B. fragilis* under aerobic environment in a temperature range of 30-40° C. Such a temperature range is, from the viewpoint of growth rate of *B. fragilis*, preferably 32-39° C. more preferably 34-39° C., and particularly preferably 35-37° C. Such culturing is carried out for, from the viewpoint of growth amount of *B. fragilis*, preferably 16-72 h, more preferably 16-50 h, and particularly preferably from 30-48 h. Upon storage of the medium of the present invention, when the medium of the present invention is a semi-fluid medium containing agar, from the viewpoint of long-term storage, the present medium is stored by preferably refrigeration at 2-10° C., more preferably refrigeration at 2-9° C., and particularly preferably refrigeration at 2-8° C. When the medium of the present invention is a liquid medium, from the viewpoint of long-term storage, the present medium is stored by preferably freezing at −4 to −80° C., more preferably freezing at −4 to −40° C., and particularly preferably freezing at −10 to −20° C.

<Detection Method of *B. fragilis*>

In the method of detecting *B. fragilis* of the present invention, for example as *B. fragilis* grows, amino acids contained in the medium of the present invention are consumed and the pH of the medium changes from neutral to basic, resulting in the color change of an acid-base indicator, and *B. fragilis* can be easily detected from this color change. For example, when using neutral red as the acid-base indicator in the medium of the present invention, when the pH changes from neutral to basic, the color of said medium changes from red to yellow, and *B. fragilis* can be easily detected from such color change.

As a sample that can be used in the present invention, any samples that possibly contain *B. fragilis* can be used, such as biological samples derived from feces or perianal or rectal inner wall of a human or animal, or environmental samples derived from any locations in a hospital, foods, drinks and tap water, etc.; preferably, the sample is feces that is easy to collect or foods. Methods for collecting these specimens are not particularly limited, and any known methods may be employed.

<Diagnosis Method of Disease Associated with *B. fragilis*>

The present invention also encompasses a method of diagnosing or a method to provide useful information for diagnosis, comprising at least a step of selectively growing *B. fragilis* by contacting the medium of the invention with biological samples. With such methods, by determining presence/absence of *B. fragilis* in a sample, for example, it is possible to diagnose if the cause of the disease is *B. fragilis* or not.

<Preparation Method of Medium for *H. pylori* of the Present Invention and Method to Use the Same>

The medium of the present invention can be prepared as follows: similar to ordinary culture media, each of the components except antibacterial agents that are said to be weak to heat is dissolved in water, etc., steam sterilized, and cooled to a suitable temperature; then antibacterial agents and others are added thereto. Samples can be inoculated directly to the medium of the present invention. The medium of the present invention can culture *H. pylori* under aerobic environment in a temperature range of 30-40° C. Such a temperature range is, from the viewpoint of growth rate of *H. pylori*, preferably 32-39° C., more preferably 34-39° C., and particularly preferably 35-37° C. Such culturing is carried out for, from the viewpoint of growth amount of *H. pylori*, preferably 72-192 h, more preferably 86-192 h, and particularly preferably from 110-192 h. Upon storage of the medium of the present invention, when the medium of the present invention is a semi-fluid medium containing agar, from the viewpoint of long-term storage, the present medium is stored by preferably refrigeration at 2-10° C., more preferably refrigeration at 2-9° C., and particularly preferably refrigeration at 2-8° C. When the medium of the present invention is a liquid medium, from the viewpoint of long-term storage, the present medium is stored by preferably freezing at −4 to −80° C. more preferably freezing at −4 to −40° C. and particularly preferably freezing at −10 to −20° C.

<Detection Method of *H. pylori*>

In the method of detecting *H. pylori* of the present invention, for example as *H. pylori* grows, turbidity of the medium and presence of a mass of bacteria can be visually confirmed.

As a sample that can be used in the present invention, any samples that possibly contain *H. pylori* can be used, such as biological samples derived from gastric fluid of a human. Methods for collecting these specimens are not particularly limited, and any known methods may be employed.

<Diagnosis Method of Disease Associated with *H. pylori*>

The present invention also encompasses a method of diagnosing or a method to provide useful information for diagnosis, comprising at least a step of selectively growing *H. pylori* by contacting the medium of the invention with biological samples. With such methods, by determining presence/absence of *H. pylori* in a sample, for example, it is possible to diagnose if eradication of *H. pylori* is required or not, or to provide information necessary for diagnosis.

Hereinafter, the present invention is explained in more detail with reference to examples; however, the present invention is not limited to these examples.

EXAMPLES

Example 1

To a medium according to Table 1 (without dithiothreitol), dithiothreitol was added at each concentration shown in Table 2 to prepare respective media. Specifically, peptone, sugars, salts, agar, a reducing agent, a growth-supporting agent and an acid-base indicator as shown in Table 1 were dissolved with stirring in 1000 mL of pure water, and dithiothreitol at each concentration was added, and the resulting sample was incubated at 121° C. for 15 min. After cooling to 50° C., the antibacterial agents shown in Table 1 were added and dissolved with stirring, then 8 mL each of the sample was put in containers with a lid. Then, *C. difficile* was suspended in sterile physiological saline and the suspension was inoculated to each medium such that the amount of *C. difficile* became approximately 1×10 cfu. Each medium was incubated at 37° C. for 24 h. A degree of growth of *C. difficile* was determined by 4 levels of "yellow coloration degree" (0=remains red; 1=a slight mass of bacteria was seen; 2=a mass of bacteria exhibited yellow color, 3=a mass of bacteria and the surrounding medium exhibited yellow color). Table 2 shows results of the determination.

TABLE 1

Composition of medium without dithiothreitol.

| | Component | | Concentration |
|---|---|---|---|
| Basal medium | Peptone | Peptone | 27.5 g/L |
| | Sugars | Glucose | 2.0 g/L |
| | | Mannitol | 6.0 g/L |
| | Salts | Sodium chloride | 5.0 g/L |
| | | Potassium dihydrogen phosphate | 1.0 g/L |
| | | Disodium hydrogen phosphate | 5.0 g/L |
| | | Sodium taurocholate | 0.5 g/L |
| | Antibacterial agent | Cycloserine | 250 mg/L |
| | | Cefoxitin | 8.0 mg/L |
| | Optional components | Agar | 1.0 g/L |
| | | Neutral red [acid-base indicator] | 20.0 mg/L |
| | | Cysteine [reducing agent] | 1.0 g/L |
| Growth supporting agent | First | Glycine | 1.0 g/L |
| | | Magnesium sulfate | 0.1 g/L |
| | Second | Arginine | 1.0 g/L |
| | | Sodium sulfite | 0.1 g/L |

TABLE 2

Concentration of dithiothreitol added and exhibition of yellow color due to growth of *C. difficile*.

| | Concentration of dithiothreitol added (g/L) | | | | | | | |
|---|---|---|---|---|---|---|---|---|
| | 0.075 | 0.16 | 0.32 | 0.60 | 0.90 | 1.2 | 1.5 | 1.8 |
| Yellow coloration degree | 1 | 2 | 2 | 3 | 3 | 2 | 1 | 0 |

As shown in Table 2, at the concentration of 0.075-1.5 g/L of dithiothreitol added, a mass of bacteria was found; at the concentration of 0.16-1.2 g/L, a mass of bacteria exhibited yellow color, and at the concentration of 0.6 g/L and 0.9 g/L, a mass of bacteria and the surrounding medium exhibited yellow color. Therefore, the concentration of dithiothreitol to be added is, from the viewpoint of growth-supporting ability for *C. difficile*, preferably 0.075-1.5 g/L, more preferably 0.16-1.2 g/L, and particularly preferably 0.6-0.9 g/L.

In addition, to the medium according to Table 1, ascorbic acid was added at each concentration shown in Table 3 to prepare respective media. Peptone, sugars, salts, agar, a reducing agent, a growth-supporting agent and an acid-base indicator as shown in Table 1 were dissolved with stirring in 1000 mL of pure water, and ascorbic acid at each concentration was added, and the resulting sample was incubated at 121° C. for 15 min. After cooling to 50° C., antibacterial agents were added and dissolved with stirring, then 8 mL each of the sample was put in containers with a lid. Then, *C. difficile* was suspended in sterile physiological saline and the suspension was inoculated to each medium such that the amount of *C. difficile* became approximately 1×10 cfu. Each medium was incubated at 37° C. for 24 h, and the degree of growth of *C. difficile* was determined with the above 4 levels. Table 3 shows results of the determination.

TABLE 3

Concentration of ascorbic acid added and exhibition of yellow color due to growth of *C. difficile*.

| | Concentration of ascorbic acid added (g/L) | | | | | | | |
|---|---|---|---|---|---|---|---|---|
| | 0.075 | 0.16 | 0.32 | 0.64 | 1.8 | 2.7 | 3.6 | 4.5 |
| Yellow coloration degree | 1 | 2 | 3 | 3 | 3 | 2 | 1 | 0 |

As shown in Table 3, at the concentration of 0.075-3.6 g/L of ascorbic acid added, a mass of bacteria was found; at the concentration of 0.16-2.7 g/L, a mass of bacteria exhibited yellow color, and at the concentration of 0.32-1.8 g/L, a mass of bacteria and the surrounding medium exhibited yellow color. Therefore, the concentration of ascorbic acid to be added is, from the viewpoint of growth-supporting ability for *C. difficile*, preferably 0.075-3.6 g/L, more preferably 0.16-2.7 g/L, and particularly preferably 0.32-1.8 g/L.

Next, in Examples 2 to 4 and Comparative Example 1, media were prepared.

Example 2

The medium of Example 2 having the medium composition described in Table 4 was prepared as follows. Peptone, sugars, salts, agar, a reducing agent, growth-supporting agents and an acid-base indicator were dissolved with stirring in 1000 mL of pure water, and incubated at 121° C. for 15 min. After cooling to 50° C., antibacterial agents were added and dissolved with stirring, then 8 mL each of the sample was put in containers with a lid.

TABLE 4

Composition of medium of Example 2.

| | Component | | Concentration |
|---|---|---|---|
| Basal medium | Peptone | Peptone | 27.5 g/L |
| | Sugars | Glucose | 2.0 g/L |
| | | Mannitol | 6.0 g/L |
| | Salts | Sodium chloride | 5.0 g/L |
| | | Potassium dihydrogen phosphate | 1.0 g/L |
| | | Disodium hydrogen phosphate | 5.0 g/L |
| | | Sodium taurocholate | 0.5 g/L |
| | Antibacterial agent | Cycloserine | 250 mg/L |
| | | Cefoxitin | 8.0 mg/L |
| | Optional components | Agar | 1.0 g/L |
| | | Neutral red [acid-base indicator] | 20.0 mg/L |
| | | Cysteine [reducing agent] | 1.0 g/L |
| Reducing agent | | Dithiothreitol | 0.9 g/L |
| Growth supporting agent | First | Glycine | 1.0 g/L |
| | | Magnesium sulfate | 0.1 g/L |
| | Second | Arginine | 1.0 g/L |
| | | Sodium sulfite | 0.1 g/L |

Example 3

The medium was prepared in the same manner as in Example 2, except that 1.0 g/L of ascorbic acid was used instead of 0.9 g/L of dithiothreitol.

Example 4

The medium was prepared in the same manner as in Example 2, except that 1.0 g/L of tris(2-carboxyethyl) phosphine hydrochloride was further added.

Comparative Example 1

The medium was prepared in the same manner as in Example 2, except that 1.0 g/L of sodium thioglycolate was used instead of 0.9 g/L of dithiothreitol.

Comparative Example 2

The medium of Comparative Example 2 (medium for culturing *C. diffcile* under aerobic environment described in Non-Patent Literature 5) having the medium composition described in Table 5 was prepared as follows. Peptones (peptone and meat peptone), sugars (glucose and mannitol), salts (sodium chloride and sodium hydrogen carbonate), agar, reducing agents (cysteine and sodium thioglycolate), third growth-supporting agents (vitamin K and hemin) and an acid-base indicator (neutral red) were dissolved with stirring in pure water, and incubated at 121° C. for 15 min. After cooling to 50° C. sodium taurocholate (salts), cycloserine and cefoxitin (antibacterial agents) and lysozyme (third growth-supporting agent) dissolved in sterile pure water were added and stirred. Then, the sample was dispensed in containers with a lid.

TABLE 5

Composition of medium of Comparative Example 2.

| | | Component | Concentration |
|---|---|---|---|
| Basal medium | Peptone | Peptone | 10.0 g/L |
| | | Meat peptone | 5.0 g/L |
| | Sugars | Glucose | 10.0 g/L |
| | | Mannitol | 6.0 g/L |
| | Salts | Sodium chloride | 5.0 g/L |
| | | Sodium hydrogen carbonate | 0.1 g/L |
| | | Sodium taurocholate | 0.5 g/L |
| | Antibacterial agent | Cycloserine | 250 mg/L |
| | | Cefoxitin | 16.0 mg/L |
| | Optional components | Agar | 1.0 g/L |
| | | Neutral red [acid-base indicator] | 50.0 mg/L |
| | | Cysteine [reducing agent] | 1.0 g/L |
| | | Sodium thioglycolate [reducing agent] | 1.0 g/L |
| Third growth supporting agent | | Vitamin K | 1.0 mg/L |
| | | Hemin | 5.0 mg/L |
| | | Lysozyme | 5.0 mg/L |

<Storage Stability Test of Each Medium>

Each of the media of Examples 2 to 4 and Comparative Examples 1 and 2 immediately after preparation were stored at 2-8° C. for a period of 0, 0.5, 1, 2, 3 or 4 months. After such storage, *C. difficile* was suspended in sterile physiological saline and the suspension was inoculated to each medium such that the amount of *C. difficile* became approximately $1\times10^6$ cfu. The media of Examples 2 to 4 and Comparative Example 1 were incubated at 37° C. for 24 h, and the medium of comparative Example 2 was incubated at 37° C. for 72 h. After the incubation, growth of *C. difficile* was determined from the color of each medium and/or presence/absence of a mass of bacteria.

As a result, as shown in Table 6, while *C. difficile* grew on any of the media of Examples 2 to 4 stored for 0-4 months, *C. difficile* did not grow on the media of Comparative Examples 1 and 2 stored for 0.5 months or longer (in Table 6, those that grew are marked by "○", and those that did not grow are marked by "x"). Therefore, it has been shown that while the media of Examples 2 to 4 maintain the detection sensitivity for *C. difficile* even after at least 4 months of storage from the preparation, the media of Comparative Examples 1 and 2 lose the detection sensitivity for *C. difficile* after 0.5 month or more of storage from the preparation. Furthermore, when comparing the composition of each medium, it has been shown that, as the reducing agent, the use of dithiothreitol or ascorbic acid, or dithiothreitol and tris(2-carboxyethyl)phosphine hydrochloride, rather than the use of sodium thioglycolate, can significantly improve quality-retaining period of the media without losing detection sensitivity for *C. difficile*.

TABLE 6

Presence/absence of growth of *C. difficile* on each medium stored for various periods of time.

| | | Storage period | | | | | |
|---|---|---|---|---|---|---|---|
| Medium | | 0 month | 0.5 months | 1 months | 2 months | 3 months | 4 months |
| Example | 2 | ○ | ○ | ○ | ○ | ○ | ○ |
| | 3 | ○ | ○ | ○ | ○ | ○ | ○ |
| | 4 | ○ | ○ | ○ | ○ | ○ | ○ |
| Comparative Example | 1 | ○ | x | x | x | x | x |
| | 2 | ○ | x | x | x | x | x |

<Growth-Supporting Ability Test for *C. difficile* of Each Medium>

(1) Medium Immediately after Preparation

*C. difficile* was suspended in sterile physiological saline, and the suspension was inoculated to the media of Examples 2 to 4 and Comparative Examples 1 and 2 immediately after preparation such that the amount of *C. difficile* became about 500, 50, 5 or 0 cfu. The media of Examples 2 to 4 and Comparative Example 1 were incubated at 37° C. for 24 h, and the medium of Comparative Example 2 was incubated at 37° C. for 72 h. After the incubation, presence/absence of the growth of *C. difficile* was determined from the color of each medium and/or presence/absence of a mass of bacteria.

As a result, as shown in Table 7, while *C. difficile* grew on any of the media of Examples 2 to 4 and Comparative Example 1 with 500-5 cfu of inoculation, *C. difficile* did not grow on the media of Comparative Example 2 with any inoculum doses (in Table 7, those that grew are marked by "○", and those that did not grow are marked by "x"). Accordingly, the media of Examples 2 to 4 were shown to have significantly higher detection sensitivity for *C. difficile* than the medium of Comparative Example 2. Furthermore, when comparing the composition of each medium, glycine, magnesium sulfate, arginine and/or sodium sulfite were suggested to serve as a good growth-supporting agent of *C. difficile*.

TABLE 7

Presence/absence of growth of *C. difficile* on each medium immediately after preparation.

| Medium | | Inoculum dose (cfu) | | | |
|---|---|---|---|---|---|
| | | 500 | 50 | 5 | 0 |
| Example | 2 | o | o | o | x |
| | 3 | o | o | o | x |
| | 4 | o | o | o | x |
| Comparative Example | 1 | o | o | o | x |
| | 2 | x | x | x | x |

(2) Media that have been Stored for 0.5 Months after Preparation

The media of Examples 2 to 4 and Comparative Examples 1 and 2 after respective preparation were stored at 2-8° C. for 0.5 months. *C. difficile* was suspended in sterile physiological saline, and the suspension was inoculated to the media such that the amount of *C. difficile* became about 800, 80, 8 or 0 cfu. The media of Examples 2 to 4 and Comparative Example 1 were incubated at 37° C. for 24 h, and the medium of Comparative Example 2 was incubated at 37° C. for 72 h. Then, the media were visually checked to determine presence/absence of the growth from the color of the media and/or presence/absence of a mass of bacteria.

As a result, as shown in Table 8, while *C. difficile* grew on the media of Examples 2 to 4 with 800-8 cfu of inoculation, *C. difficile* did not grow on the media of Comparative Examples 1 and 2 with any inoculum doses (in Table 8, those that grew are marked by "o", and those that did not grow are marked by "x"). Accordingly, the media of Examples 2 to 4 were shown to have higher detection sensitivity for *C. difficile* than the media of Comparative Examples 1 and 2. In addition, when comparing the composition of each medium, glycine, magnesium sulfate, arginine and/or sodium sulfite were suggested to serve as a good growth-supporting agent of *C. difficile*. Furthermore, the media of Examples 2 to 4 were shown to have an ability to make several cfu of *C. difficile* grow.

TABLE 8

Presence/absence of growth of *C. difficile* on each medium stored for 0.5 months from preparation.

| Medium | | Inoculum dose (cfu) | | | |
|---|---|---|---|---|---|
| | | 800 | 80 | 8 | 0 |
| Example | 2 | o | o | o | x |
| | 3 | o | o | o | x |
| | 4 | o | o | o | x |
| Comparative Example | 1 | x | x | x | x |
| | 2 | x | x | x | x |

<Comparison of Growth-Supporting Ability of Media of Example 2 and Comparative Example 2>

*C. difficile* was cultured under anaerobic environment using a GAM medium (Nissui Pharmaceutical Co., Ltd.) supplemented with 0.5 g/L of taurocholic acid, then the resulting colonies were suspended in sterile physiological saline, and the suspension was serially diluted by 10 times with sterile physiological saline. Such diluted suspensions were inoculated respectively into the media of Example 2 and Comparative Example 2 immediately after preparation and the above-mentioned GAM medium. The medium of Examples 2 was incubated at 37° C. for 20 h, the medium of Comparative Example 2 was incubated at 37° C. for 72 h, and the GAM medium was incubated under anaerobic environment at 37° C. for 24 h. After the incubation, presence/absence of the growth of *C. difficile* was determined from the color of each medium and presence/absence of a mass of bacteria. Each inoculum dose was determined from the number of colonies formed on the GAM medium.

Figure 2A:
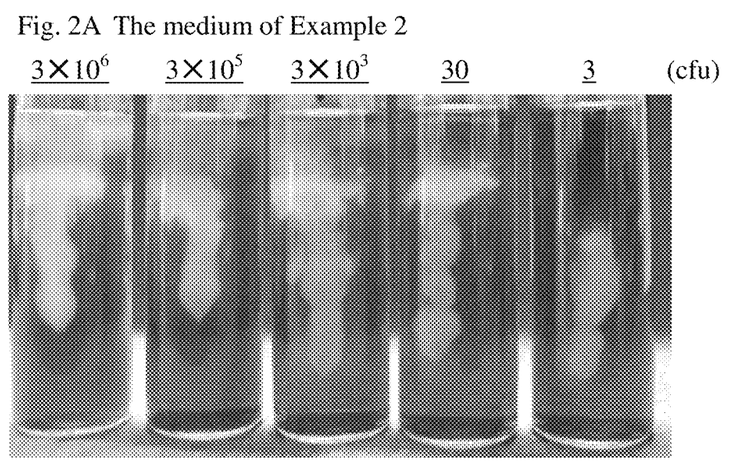
FIGS. 2A and 2B show the medium of Example 2 (FIG. 2A) and the medium of Comparative Example 2 (FIG. 2B) after culturing C. difficile under aerobic environment, which has been inoculated to each of the medium immediately after preparation at a respective amount. Numbers in the figure indicate the amounts of inoculated bacteria (cfu).
Figure 2B:
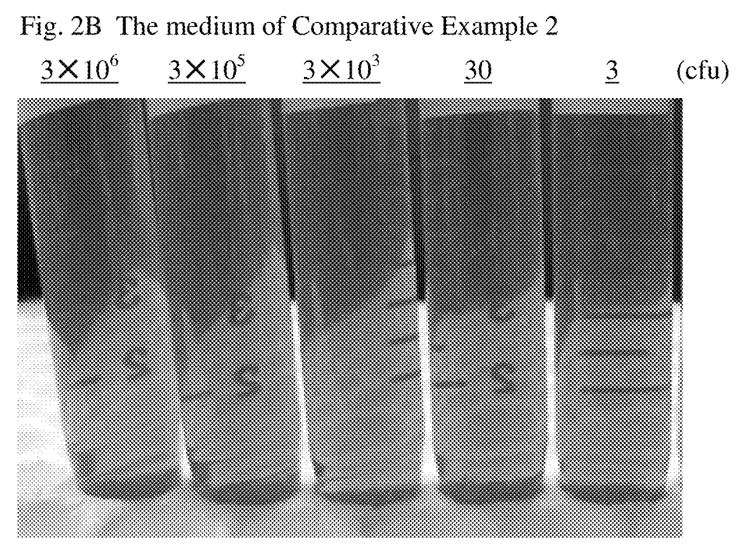

As a result, as shown in Table 9 and FIGS. 2A and 2B, *C. difficile* grew on the medium of Example 2 with $3-3 \times 10^6$ cfu of inoculation, whereas in the case of the medium of Comparative Example 2, *C. difficile* grew only on the media with the inoculum dose of $3 \times 10$ and $3 \times 10^6$ (in Table 9, those that grew are marked by "c", and those that did not grow are marked by "x"). Accordingly, the medium of Example 2 was shown to have significantly higher detection sensitivity for *C. difficile* than the medium of Comparative Example 2. In addition, when comparing the composition of each medium, glycine, magnesium sulfate, arginine and/or sodium sulfite were suggested to serve as a good growth-supporting agent of *C. diffcile*.

TABLE 9

Presence/absence of growth of *C. difficile* upon inoculation of various inoculum doses.

| Medium | Inoculum dose (cfu) | | | | |
|---|---|---|---|---|---|
| | $3 \times 10^6$ | $3 \times 10^5$ | $3 \times 10^3$ | 30 | 3 |
| Example 2 | o | o | o | o | o |
| Comparative Example 2 | o | o | x | x | x |

<Comparison of Growth of Each Isolate in Each Medium>

Isolates were cultured using a GAM medium (Nissui Pharmaceutical Co., Ltd.) supplemented with 0.5 g/L of taurocholic acid under anaerobic environment for 24 h. The resulting cultured isolates were suspended in sterile physiological saline such that the turbidity became equivalent to a 0.5 McFarland standard, and they were used as test bacterial solutions. Each test bacterial solution was inoculated to the media of Examples 2 to 4 and Comparative Example 1 immediately after preparation, by puncturing into the media using a disposable loop with a retaining volume equivalent to 10 μL, and also the test bacterial solutions were smeared on a GAM medium supplemented with 0.5 g/L of taurocholic acid as a control medium.

Each of the bacterial strains was subjected to the tests; the media of Examples 2 to 4 and Comparative Example 1 were cultured under aerobic environment at 37° C. for 24 h, and the above GAM medium was cultured under anaerobic environment at 37° C. for 24 h. Table 10 shows results of visual confirmation of growth. It is to be noted that facultative anaerobic bacteria refer to bacteria that can grow in the presence or absence of oxygen.

TABLE 10

Presence/absence of growth of each bacterial strain upon its inoculation on each medium.

| | | | Example | | | Com. | Control |
|---|---|---|---|---|---|---|---|
| | Isolate | | 2 | 3 | 4 | Ex. 1 | medium |
| C. difficile | ATCC9689 | Obligate | o | o | o | o | o |
| | ATCC43255 | anaerobic | o | o | o | o | o |
| | ATCC700057 | bacteria | o | o | o | o | o |
| | Clinical isolate 1 | | o | o | o | o | o |
| C. perfringens | ATCC13124 | | x | x | x | x | o |
| B. fragilis | ATCC25285 | | x | x | x | x | o |
| E. coli | ATCC25922 | Faculta- | x | x | x | x | o |
| | Clinical isolate 2 | tive anaerobic | x | o | x | o | o |
| E. aerogenes | ATCC13048 | bacteria | x | x | x | x | o |
| | Clinical isolate 3 | | x | o | x | o | o |
| L. casei | ATCC393 | | x | x | x | x | o |
| | Clinical isolate 4 | | x | x | x | x | o |
| E. faecium | ATCC6959 | | x | x | x | x | o |
| | Clinical isolate 5 | | x | x | x | x | o |

While C. difficile grew on all media, E. coli clinical isolate 2 and E. aerogenes clinical isolate 3 grew on the media of Example 3, Comparative Example 1 and the control medium. Since the media on which the E. Coli clinical isolate 2 and the E. aerogenes clinical isolate 3 have grown exhibited red color, they can be clearly distinguished from each of the media on which C. difficile have grown and which exhibits yellow color. The reason is considered as follow: when the E. coli clinical isolate 2 and E. aerogenes clinical isolate 3 grew, sugar was metabolized by glycolysis to generate pyruvic acid, and the pyruvic acid was reduced to generate lactic acid, thereby changing the media's pH from neutral to acidic and the acid-base indicator neutral red did not change its color. In addition, in the media of Examples 2 and 4 comprising dithiothreitol, the E. coli clinical isolate 2 and the E. aerogenes clinical isolate 3 did not grew; this suggests that dithiothreitol has a growth suppressing ability for those strains.

Example 5

The medium of Example 5 having the medium composition described in Table 11 was prepared as follows. It was prepared in the same manner as in Example 2, except that fructose was used instead of mannitol, 0.45 g/L of dithiothreitol was used instead of 0.9 g/L, and as an antibacterial agent, cefoxitin was not used, but 400 mg/L of cycloserine was used instead of 250 mg/L. Specifically, peptone, sugars, salts, agar, a reducing agent, growth-supporting agents and an acid-base indicator were dissolved with stirring in 1000 mL of pure water, and incubated at 121° C. for 15 min. After cooling to 50° C., the antibacterial agent was added and dissolved with stirring, then 8 mL each of the sample was put in containers with a lid.

TABLE 11

Composition of medium of Example 5.

| Component | | | Concentration |
|---|---|---|---|
| Basal medium | Peptone | Peptone | 27.5 g/L |
| | Sugars | Glucose | 2.0 g/L |
| | | Fructose | 6.0 g/L |
| | Salts | Sodium chloride | 5.0 g/L |
| | | Potassium dihydrogen phosphate | 1.0 g/L |
| | | Disodium hydrogen phosphate | 5.0 g/L |
| | | Sodium taurocholate | 0.5 g/L |
| | Antibacterial agent | Cycloserine | 400 mg/L |
| | Optional components | Agar | 1.0 g/L |
| | | Neutral red [acid-base indicator] | 20.0 mg/L |
| | | Cysteine [reducing agent] | 1.0 g/L |
| Reducing agent | | Dithiothreitol | 0.45 g/L |
| Growth supporting agent | First | Glycine | 1.0 g/L |
| | | Magnesium sulfate | 0.1 g/L |
| | Second | Arginine | 1.0 g/L |
| | | Sodium sulfite | 0.1 g/L |

Example 6

The medium was prepared in the same manner as in Example 5, except that 1.0 g/L of ascorbic acid was used instead of 0.45 g/L of dithiothreitol.

Example 7

The medium was prepared in the same manner as in Example 5, except that 1.0 g/L of tris(2-carboxyethyl) phosphine hydrochloride was further added.

<Storage Stability Test of Media>

Each of the media of Examples 5 to 7 after preparation were stored at 2-8° C. for a period of 0, 0.5, 1, 2, 3 or 4 months. After such storage, C. perfringens was suspended in sterile physiological saline and the suspension was inoculated to each medium such that the amount of C. perfringens became approximately $1 \times 10^3$ cfu. Each medium was incubated under aerobic environment for 24 h. After the incubation, presence/absence of the growth of C. perfringens was determined from the color of the media and/or presence/absence of a mass of bacteria.

As a result, as shown in Table 12, C. perfringens grew on any of the media of Examples 5 to 7 stored for 0-4 months (in the table, those that grew are marked by "○"). Therefore, it has been shown that the media of Examples 5 to 7 maintain the detection sensitivity for *C. perfringens*, even after at least 4 months of storage from preparation.

TABLE 12

Presence/absence of growth of *C. perfringens* on the media stored for various periods of time.

| Medium | | Storage period 0 month | 0.5 months | 1 months | 2 months | 3 months | 4 months |
|---|---|---|---|---|---|---|---|
| Example | 5 | ○ | ○ | ○ | ○ | ○ | ○ |
| | 6 | ○ | ○ | ○ | ○ | ○ | ○ |
| | 7 | ○ | ○ | ○ | ○ | ○ | ○ |

<Growth-Supporting Ability>

*C. perfringens* was cultured under anaerobic environment using a GAM medium (Nissui Pharmaceutical Co., Ltd.), then the resulting colonies were suspended in sterile physiological saline, and the suspension was serially diluted by 10 times with sterile physiological saline. Such diluted suspensions were inoculated respectively into the media of Examples 5 to 7 and the above-mentioned GAM medium. The media of Examples 5 to 7 were incubated at 37° C. for 24 h, and the GAM medium was incubated at 37° C. for 24 h. After the incubation, presence/absence of the growth of *C. perfringens* was determined from the color of the media and/or presence/absence of a mass of bacteria. Each inoculum dose was determined from the number of colonies formed on the GAM medium.

As a result, as shown in Table 13, *C. perfringens* grew on the media of Examples 5 to 7 with 3-3×$10^6$ cfu of inoculation (in the table, those that grew are marked by "n"). Therefore, the media of Examples 5 to 7 have been shown to have an ability to make several cfu of *C. perfringens* grow.

TABLE 13

Presence/absence of growth of *C. perfringens* upon inoculation of various inoculum doses.

| Medium | | Inoculum dose (cfu) | | | | |
|---|---|---|---|---|---|---|
| | | $3 \times 10^6$ | $3 \times 10^5$ | $3 \times 10^3$ | 30 | 3 |
| Example | 5 | ○ | ○ | ○ | ○ | ○ |
| | 6 | ○ | ○ | ○ | ○ | ○ |
| | 7 | ○ | ○ | ○ | ○ | ○ |

<Test Using Isolates>

Isolates were cultured using a GAM medium (Nissui Pharmaceutical Co., Ltd.) supplemented with 0.5 g/L of taurocholic acid under anaerobic environment for 24 h. The resulting cultured isolates were suspended in sterile physiological saline such that the turbidity became equivalent to a 0.5 McFarland standard, and they were used as test bacterial solutions. Each test bacterial solution was inoculated to the media of Examples 5 to 7 immediately after preparation, by puncturing into the media using a disposable loop with a retaining volume equivalent to 10 μL, and the test bacterial solutions were also smeared on the GAM medium supplemented with 0.5 g/L of taurocholic acid as a control medium.

Each of the bacterial strains was subjected to the tests; the media of Examples 5 to 7 were cultured under aerobic environment at 37° C. for 24 h, and the above GAM medium was cultured under anaerobic environment at 37° C. for 48 h. Table 14 shows results of visual confirmation of growth (in the table, those that grew are marked by "○", and those that did not grow are marked by "x").

TABLE 14

Presence/absence of growth of each bacterial isolate upon its inoculation on each medium.

| Isolate | | | Example | | | Control |
|---|---|---|---|---|---|---|
| | | | 5 | 6 | 7 | medium |
| *C. perfringens* | ATCC13124 | Obligate | ○ | ○ | ○ | ○ |
| | Clinical isolate 6 | anaerobic | ○ | ○ | ○ | ○ |
| *C. difficile* | ATCC9689 | bacteria | x | x | x | ○ |
| *B. fragilis* | ATCC25285 | | x | x | x | ○ |
| *E. coli* | ATCC25922 | Facultative | x | x | x | ○ |
| *E. aerogenes* | ATCC13048 | anaerobic | x | x | x | ○ |
| *L. casei* | ATCC393 | bacteria | x | x | x | ○ |
| *E. faecium* | ATCC6959 | | x | x | x | ○ |

Example 8

The medium of Example 8 having the medium composition described in Table 15 was prepared as follows. The medium was prepared in the same manner as in Example 2, except that fructose was used instead of mannitol as a sugar, sodium taurocholate as a salt was not added, and vancomycin (5 mg/L) and gentamicin (20 mg/L) were used as antibacterial agents instead of cycloserine and cefoxitin.

Specifically, peptone, sugars, salts, agar, a reducing agent, growth-supporting agents and an acid-base indicator were dissolved with stirring in 1000 mL of pure water, and incubated at 121° C. for 15 min. After cooling to 50° C., antibacterial agents were added and dissolved with stirring, then 8 mL each of the sample was put in containers with a lid.

TABLE 15

Composition of medium of Example 8.

| Component | | | Concentration |
|---|---|---|---|
| Basal medium | Peptone | Peptone | 27.5 g/L |
| | Sugars | Glucose | 2.0 g/L |
| | | Fructose | 6.0 g/L |
| | Salts | Sodium chloride | 5.0 g/L |
| | | Potassium dihydrogen phosphate | 1.0 g/L |
| | | Disodium hydrogen phosphate | 5.0 g/L |
| | Antibacterial agent | Vancomycin | 5 mg/L |
| | | Gentamicin | 20 mg/L |
| | Optional components | Agar | 1.0 g/L |
| | | Neutral ref [acid-base indicator] | 20.0 mg/L |
| | | Cysteine [reducing agent] | 1.0 g/L |
| Reducing agent | | Dithiothreitol | 0.9 g/L |
| Growth supporting agent | First | Glycine | 1.0 g/L |
| | | Magnesium sulfate | 0.1 g/L |
| | Second | Arginine | 1.0 g/L |
| | | Sodium sulfite | 0.1 g/L |

Example 9

The medium was prepared in the same manner as in Example 8, except that 1.0 g/L of ascorbic acid was used instead of 0.9 g/L of dithiothreitol.

Example 10

The medium was prepared in the same manner as in Example 8, except that 0.5 g/L of tris(2-carboxyethyl) phosphine hydrochloride was further added.

<Storage Stability Test of Media>

Each of the media of Examples 8 to 10 after preparation were stored at 2-8° C. for a period of 0, 0.5, 1, 2, 3 or 4 months. After such storage, *B. fragilis* was suspended in sterile physiological saline and the suspension was inoculated to each medium such that the amount of *B. fragilis* became approximately 1×10³ cfu. Each medium was incubated at 37° C. for 24 h, and presence/absence of the growth of *B. fragilis* was determined from the color of the media and/or presence/absence of a mass of bacteria.

As a result, as shown in Table 16, *B. fragilis* grew on any of the media of Examples 8 to 10 stored for 0-4 months (in the table, those that grew are marked by "○"). Therefore, it has been shown that the media of Examples 8 to 10 maintain the detection sensitivity for *B. fragilis*, even after at least 4 months of storage from preparation.

TABLE 16

Presence/absence of growth of *B. fragilis* on the media stored for various periods of time.

| | Storage period | | | | | |
|---|---|---|---|---|---|---|
| Medium | 0 month | 0.5 months | 1 months | 2 months | 3 months | 4 months |
| Example 8 | ○ | ○ | ○ | ○ | ○ | ○ |
| 9 | ○ | ○ | ○ | ○ | ○ | ○ |
| 10 | ○ | ○ | ○ | ○ | ○ | ○ |

<Growth-Supporting Ability>

*B. fragilis* was cultured under anaerobic environment using a GAM medium (Nissui Pharmaceutical Co., Ltd.), then the resulting colonies were suspended in sterile physiological saline, and the suspension was serially diluted by 10 times with sterile physiological saline. Such diluted suspensions were inoculated respectively into the media of Examples 8 to 10 immediately after preparation and the above GAM medium. The media of Examples 8 to 10 were incubated at 37° C. for 24 h, and the GAM medium was incubated at 37° C. for 24 h. After the incubation, presence/absence of the growth of *B. fragilis* was determined from the color of the media and/or presence/absence of a mass of bacteria. Each inoculum dose was determined from the number of colonies formed on the GAM medium.

As a result, as shown in Table 17. *B. fragilis* grew on any of the media of Examples 8 to 10 on which 9-9×10⁶ cfu were inoculated (in the table, those that grew are marked by "○", and those that did not grow are marked by "x"). Therefore, the media of Examples 8 to 10 have been shown to have an ability to make several cfu of *B. fragilis* grow.

TABLE 17

Presence/absence of growth of *B. fragilis* upon inoculation of various inoculum doses.

| | Inoculum dose (cfu) | | | | |
|---|---|---|---|---|---|
| Medium | 9 × 10⁶ | 9 × 10⁵ | 9 × 10³ | 90 | 9 |
| Example 8 | ○ | ○ | ○ | ○ | ○ |
| 9 | ○ | ○ | ○ | ○ | ○ |
| 10 | ○ | ○ | ○ | ○ | ○ |

<Test Using Isolates>

Isolates were cultured using a GAM medium (Nissui Pharmaceutical Co., Ltd.) supplemented with 0.5 g/L of taurocholic acid under anaerobic environment for 24 h. The resulting cultured isolates were suspended in sterile physiological saline such that the turbidity became equivalent to a 0.5 McFarland standard, and they were used as test bacterial solutions. Each test bacterial solution was inoculated to the media of Examples 8 to 10 immediately after preparation, by puncturing into the media using a disposable platinum loop with a retaining volume equivalent to 10 μL, and the test bacterial solutions were also smeared on the GAM medium as a control medium.

Each of the bacterial strains was subjected to the tests; the media of Examples 8 to 10 were cultured under aerobic environment at 37° C. for 24 h, and the above GAM medium was cultured under anaerobic environment at 37° C. for 48 h. Table 18 shows results of visual confirmation of growth (in the table, those that grew are marked by "○", and those that did not grow are marked by "x").

TABLE 18

Presence/absence of growth of each bacterial isolate upon its inoculation on each medium.

| | | | Example | | | Control |
|---|---|---|---|---|---|---|
| Isolate | | | 8 | 9 | 10 | medium |
| *B. fragilis* | ATCC25285 | Obligate | ○ | ○ | ○ | ○ |
| | Clinical isolate 7 | anaerobic | ○ | ○ | ○ | ○ |
| *C. difficile* | ATCC9689 | bacteria | x | x | x | ○ |
| *C. perfringens* | ATCC13124 | | x | x | x | ○ |
| *E. coli* | ATCC25922 | Facultative | x | x | x | ○ |
| *L. casei* | ATCC393 | anaerobic | x | x | x | ○ |
| | Clinical isolate 4 | bacteria | x | x | x | ○ |
| *E. faecium* | ATCC6959 | | x | x | x | ○ |
| | Clinical isolate 5 | | x | x | x | ○ |

In each of Examples 11 to 13, media were prepared as follows.

Example 11

The medium of Example 11 having the medium composition described in Table 19 was prepared as follows. The medium was prepared in the same manner as in Example 2, except that mannitol and sodium taurocholate were not added, vancomycin (5 mg/L), trimethoprim (2.5 mg/L) and amphotericin B (5 mg/L) were used as antibacterial agents instead of cycloserine and cefoxitin, sodium hydrogen carbonate (1.6 g/L) as a first growth-supporting agent and soluble starch (1.0 g/L) as a second growth-supporting agent (from Kanto Chemical Co., Inc., Product number: 37328-01) were further added.

Specifically, peptone, sugars, salts, agar, a reducing agent, growth-supporting agents and an acid-base indicator were dissolved with stirring in 1000 mL of pure water, and incubated at 121° C. for 15 min. After cooling to 50° C., antibacterial agents were added and dissolved with stirring, then 14 mL each of the sample was put in containers with a lid.

TABLE 19

Composition of medium of Example 11.

| | Component | | Concentration |
|---|---|---|---|
| Basal medium | Peptone | Peptone | 27.5 g/L |
| | Sugars | Glucose | 2.0 g/L |
| | Salts | Sodium chloride | 5.0 g/L |
| | | Potassium dihydrogen phosphate | 1.0 g/L |
| | | Disodium hydrogen phosphate | 5.0 g/L |
| | Antibacterial agent | Vancomycin | 5 mg/L |
| | | Trimethoprim | 2.5 mg/L |
| | | Amphotericin B | 5 mg/L |

TABLE 19-continued

Composition of medium of Example 11.

| | Component | Concentration |
|---|---|---|
| Optional components | Agar | 1.0 g/L |
| | Neutral red [acid-base indicator] | 20.0 mg/L |
| | Cysteine [reducing agent] | 1.0 g/L |
| Reducing agent | Dithiothreitol | 0.9 g/L |
| Growth supporting agent | First Glycine | 1.0 g/L |
| | Magnesium sulfate | 0.1 g/L |
| | Sodium hydrogen carbonate | 1.6 g/L |
| | Second Arginine | 1.0 g/L |
| | Sodium sulfite | 0.1 g/L |
| | Soluble starch | 1.0 g/L |

Example 12

The medium was prepared in the same manner as in Example 11, except that 1.0 g/L of ascorbic acid was used instead of 0.9 g/L of dithiothreitol.

Example 13

The medium was prepared in the same manner as in Example 11, except that 0.25 g/L of tris(2-carboxyethyl) phosphine hydrochloride was further added.

<Storage Stability Test of Media>

Each of the media of Examples 11 to 13 after preparation were stored at 2-8° C. for a period of 0, 0.5, 1, 2, 3 or 4 months. After such storage. *H. pylori* was suspended in sterile physiological saline and the suspension was inoculated to each medium such that the amount of *H. pylori* became approximately $1 \times 10^5$ cfu. The media of Examples 11 to 13 were incubated at 37° C. for 72 h, and presence/absence of the growth of *H. pylori* was determined from the turbidity of the media and/or presence/absence of a mass of bacteria.

As a result, as shown in Table 20, *H. pylori* grew on any of the media of Examples 11 to 13 stored for 0-4 months (in the table, those that grew are marked by "o"). Therefore, it has been shown that the media of Examples 11 to 13 maintain the detection sensitivity for *H. pylori*, even after at least 4 months of storage from preparation.

TABLE 20

Presence/absence of growth of *H. pylori* on the media stored for various periods of time.

| | | Storage period | | | | |
|---|---|---|---|---|---|---|
| Medium | 0 month | 0.5 months | 1 months | 2 months | 3 months | 4 months |
| Example 11 | o | o | o | o | o | o |
| 12 | o | o | o | o | o | o |
| 13 | o | o | o | o | o | o |

<Test Using Isolates>

*H. pylori* was cultured using a brain heart infusion broth (OXOID Co., Ltd.) supplemented with a horse hemolytic solution under microaerobic environment. Other isolates were cultured using a GAM medium (Nissui Pharmaceutical Co., Ltd.) under anaerobic environment for 24 h. The resulting cultured isolates were suspended in sterile physiological saline such that the turbidity became equivalent to a 0.5 McFarland standard, and they were used as test bacterial solutions. Each test bacterial solution was inoculated to the media of Examples 11 to 13 immediately after preparation, by puncturing into the media using a disposable platinum loop with a retaining volume equivalent to 10 μL, and the test bacterial solutions were also smeared on the brain heart infusion broth supplemented with a horse hemolytic solution, as a control medium.

Each of the bacterial strains was subjected to the tests; the media of Examples 11 to 13 were cultured under aerobic environment at 37° C. for 72 h. and the control medium was cultured under microaerobic environment at 37° C. for 72 h. Table 21 shows results of visual confirmation of growth (in the table, those that grew are marked by "o", and those that did not grow are marked by "x"). "Microaerobic culture" in this case was carried out under the condition that the control medium on which the test bacterial solution was smeared was encapsulated in a square-shaped jar for Anaero Pack together with Anaero Pack®-MicroAero (Mitsubishi Gas Chemical Company, Inc.).

TABLE 21

Presence/absence of growth of each bacterial isolate upon its inoculation on each medium.

| | | | Example | | | Control |
|---|---|---|---|---|---|---|
| | Isolate | | 11 | 12 | 13 | medium |
| *H. pylori* | ATCC43504 | Microaerobic bacteria | o | o | o | o |
| | Clinical isolate 8 | | o | o | o | o |
| | Clinical isolate 9 | | o | o | o | o |
| | Clinical isolate 10 | | o | o | o | o |
| | Clinical isolate 11 | | o | o | o | o |
| *C. difficile* | ATCC9689 | Obligate anaerobic bacteria | x | x | x | o |
| *C. perfringens* | ATCC13124 | | x | x | x | o |
| *E. coli* | ATCC25922 | Facultative anaerobic bacteria | x | x | x | o |
| *E. aerogenes* | ATCC13048 | | x | x | x | o |
| *L. casei* | ATCC393 | | x | x | x | o |
| | Clinical isolate 4 | | x | x | x | o |
| *E. faeciam* | ATCC6959 | | x | x | x | o |
| | Clinical isolate 5 | | x | x | x | o |
| *C. albicans* | ATCC10231 | | x | x | x | o |
| | Clinical isolate 12 | | x | x | x | o |

INDUSTRIAL APPLICABILITY

The medium of the present invention can be stored for a long period of time of at least 4 months by comprising dithiothreitol and/or ascorbic acid as a reducing agent, and therefore it enables to ensure sufficient quality-retaining period and can be commercialized and distributed on the market. In addition, easy detection of obligate anaerobic bacteria or microaerobic bacteria is possible by culturing the obligate anaerobic bacteria or microaerobic bacteria under aerobic environment using this medium. Furthermore, by adding a growth-supporting agent in this medium, it is possible to improve the detection sensitivity of obligate anaerobic bacteria or microaerobic bacteria, to prevent false negatives, and to make proper diagnosis by accurately determining whether or not the cause of a disease is obligate anaerobic bacteria or microaerobic bacteria. Meanwhile, by making this medium as a semi-fluid medium or liquid medium, subsequent to culturing obligate anaerobic bacteria or microaerobic bacteria, genes and toxins derived from the obligate anaerobic bacteria or micro-aerobic bacteria can be subjected to variety of molecular biological tests.

The invention claimed is:

1. A method comprising
    culturing obligate anaerobic bacteria or microaerobic bacteria under aerobic environment using a long-term storage medium, wherein the storage medium comprises a semi-fluid basal medium containing agar and 0.075-1.5 g/L dithiothreitol and/or 0.075-3.6 g/L ascorbic acid as a reducing agent; glycine and magnesium sulfate as a first growth-supporting agent; and arginine and sodium sulfite as a second growth-supporting agent; and
    wherein after preparing the medium and storing the medium at 2-8° C. for at least 4 months, the medium maintains its detection sensitivity for obligate anaerobic bacteria or microaerobic bacteria, when inoculated with the bacteria and incubated at 37° C. for 24-72 hours.

2. The method according to claim 1, the medium further comprising tris(2-carboxyethyl)phosphine hydrochloride as a reducing agent.

3. The method according to claim 2, wherein the concentration of tris(2-carboxyethyl)phosphine hydrochloride is 0.1-2.0 g/L.

4. The method according to claim 1, the medium further comprising sodium hydrogen carbonate as the first growth-supporting agent.

5. The method according to claim 4, wherein the concentration of sodium hydrogen carbonate is 0.5-4.0 g/L.

6. The method according to claim 1, the medium further comprising potassium sulfite, sodium pyruvate, potassium pyruvate and/or soluble starch as the second growth-supporting agent.

7. The method according to claim 6, wherein the concentration of sodium pyruvate is 0.1-2.0 g/L, and the concentration of soluble starch is 1.0-8.0 g/L.

8. The method according to claim 1, wherein the basal medium comprises at least one antibacterial agent selected from the group consisting of cycloserine, cephalosporin antibacterial agents, glycopeptide antibacterial agents, diaminopyrimidine antibacterial agents, polyene antibacterial agents, polypeptide antibacterial agents and aminoglycoside antibacterial agents.

9. The method according to claim 8, wherein the cephalosporin antibacterial agent is cefoxitin, the glycopeptide antibacterial agent is vancomycin, the diaminopyrimidine antibacterial agent is trimethoprim, the polyene antibacterial agent is amphotericin B, the polypeptide antibacterial agent is polymyxin B, and the aminoglycoside antibacterial agent is gentamicin.

10. The method according to claim 1, further comprising detecting obligate anaerobic bacteria or microaerobic bacteria.

11. The method according to claim 1, wherein the obligate anaerobic bacteria or microaerobic bacteria are obtained from biological samples and/or environmental samples.

12. The method according to claim 1, further comprising storing obligate anaerobic bacteria or microaerobic bacteria in the medium at 2-8° C. at least for a period of 0.5 months.

13. The method according to claim 1, wherein the concentration of glycine is 0.1-2.0 g/L, and the concentration of magnesium sulfate is 0.01-1.0 g/L.

14. The method according to claim 1, wherein the concentration of arginine is 0.1-2.0 g/L, and the concentration of sodium sulfite is 0.01-1.0 g/L.

* * * * *